(12) United States Patent
Young

(10) Patent No.: US 10,314,755 B2
(45) Date of Patent: Jun. 11, 2019

(54) USER-INCONTINENCE CLEANING KIT AND METHOD OF USE THEREOF

(71) Applicant: Joy Oan Young, Fort Lauderdale, FL (US)

(72) Inventor: Joy Oan Young, Fort Lauderdale, FL (US)

( * ) Notice: Subject to any disclaimer, the term of this patent is extended or adjusted under 35 U.S.C. 154(b) by 21 days.

(21) Appl. No.: 15/289,586

(22) Filed: Oct. 10, 2016

(65) Prior Publication Data
US 2017/0265959 A1    Sep. 21, 2017

Related U.S. Application Data

(60) Provisional application No. 62/309,719, filed on Mar. 17, 2016.

(51) Int. Cl.
| | |
|---|---|
| *A61F 17/00* | (2006.01) |
| *A61F 13/551* | (2006.01) |
| *A61B 50/37* | (2016.01) |
| *A61G 7/10* | (2006.01) |
| *A61B 50/31* | (2016.01) |
| *A61F 13/15* | (2006.01) |
| *A61B 50/00* | (2016.01) |

(52) U.S. Cl.
CPC ............ *A61G 7/1023* (2013.01); *A61B 50/31* (2016.02); *A61B 50/37* (2016.02); *A61F 13/551* (2013.01); *A61F 17/00* (2013.01); *A61G 7/1051* (2013.01); *A61B 2050/0056* (2016.02); *A61B 2050/311* (2016.02); *A61F 2013/15121* (2013.01); *A61F 2013/15154* (2013.01); *A61G 7/1038* (2013.01)

(58) Field of Classification Search
CPC ... A61B 50/31; A61B 50/37; A61B 2050/311; A41D 13/11; A41D 19/0075; A41D 13/1236; A61F 13/551; A61F 2013/15154; A61F 2013/15121; A61F 13/5516; A61F 13/55165; A61F 17/00; A61F 50/37
USPC .... 206/570, 440, 803; 5/484, 487, 494, 501; 128/855, 885; 604/356, 322
See application file for complete search history.

(56) References Cited

U.S. PATENT DOCUMENTS

| | | | | |
|---|---|---|---|---|
| 4,186,955 A | * | 2/1980 | Campbell | ............. E01H 1/1206 15/104.8 |
| 4,702,378 A | | 10/1987 | Finkel | |
| 4,917,238 A | | 4/1990 | Schumacher | |
| 4,923,453 A | * | 5/1990 | Bullard, Jr. | ............. A61F 5/485 128/855 |
| 5,078,709 A | * | 1/1992 | Siciliano | ........... A61F 13/00042 602/45 |
| 5,598,923 A | * | 2/1997 | Owens | ................. A61B 50/312 150/130 |
| 5,701,617 A | * | 12/1997 | Colby | ................. A47C 27/006 5/484 |
| 5,884,771 A | | 3/1999 | McCormick | |

(Continued)

*Primary Examiner* — Jacob K Ackun
*Assistant Examiner* — Jenine Pagan
(74) *Attorney, Agent, or Firm* — Mark C. Johnson; Johnson |Dalal

(57) ABSTRACT

A user-incontinence cleaning kit including at least one of a scent blocker and a facial mask, a plurality of gloves sized configured to be worn by the user in an overlapping relationship with respect to each other and corresponding to a select order of use for cleaning a patient, and a plurality of incontinence pads sized and shaped to be interposed between a backside of a patient and a top of a patient support structure.

4 Claims, 5 Drawing Sheets

(56) References Cited

U.S. PATENT DOCUMENTS

| | | | | |
|---|---|---|---|---|
| 5,931,303 A * | 8/1999 | Salvadori | A61M 25/002 | 206/363 |
| 6,233,762 B1 * | 5/2001 | Bradley | A47C 21/022 | 5/484 |
| 6,723,080 B1 | 4/2004 | Habib | | |
| 6,926,708 B1 * | 8/2005 | Franks-Farah | A61M 25/002 | 206/571 |
| 6,973,675 B2 * | 12/2005 | Cheng | A41D 19/0058 | 2/161.7 |
| 7,588,168 B2 * | 9/2009 | Bagwell | A47K 5/12 | 211/71.01 |
| 7,617,937 B1 | 11/2009 | Passarelli | | |
| 8,047,375 B1 * | 11/2011 | Hartsfield | A45C 13/02 | 206/581 |
| 8,082,612 B2 * | 12/2011 | Saunders | A47C 31/105 | 5/484 |
| 8,162,146 B2 | 4/2012 | Sherrill | | |
| 2006/0089612 A1 * | 4/2006 | Price | A61F 13/5519 | 604/385.06 |
| 2007/0248290 A1 * | 10/2007 | Melvan | B65D 33/14 | 383/43 |
| 2007/0287976 A1 * | 12/2007 | Sherrill | A61F 15/001 | 604/385.06 |
| 2008/0108965 A1 * | 5/2008 | Christensen | A61F 13/15 | 604/385.06 |
| 2009/0014351 A1 * | 1/2009 | Walker | A61F 17/00 | 206/570 |
| 2009/0260635 A1 * | 10/2009 | Dean | A41D 13/11 | 128/863 |
| 2011/0229059 A1 * | 9/2011 | Hanna | A61F 13/5512 | 383/1 |
| 2012/0204518 A1 * | 8/2012 | Jauvin | B65F 1/0006 | 53/469 |
| 2014/0237695 A1 * | 8/2014 | Al Malki | A41D 13/11 | 2/9 |

\* cited by examiner

USER-INCONTINENCE CLEANING KIT AND METHOD OF USE THEREOF

CROSS-REFERENCE TO RELATED APPLICATION

This application claims priority to U.S. Provisional Patent Application No. 62/309,719 filed Mar. 17, 2016, the entirety of which is incorporated by reference.

FIELD OF THE INVENTION

The present invention relates generally to cleaning kits, and, more particularly, relates to a user-incontinence cleaning kit and a method of use thereof for cleaning bed-ridden patients.

BACKGROUND OF THE INVENTION

There are many known systems and kits used to clean a user or patient confined to a bed or other location, wherein the user or patient has limited mobility. Although there are numerous types of kits which allow users to clean incontinent patients, little attention has been paid to effective solutions to clean the patient in a specific manner that is both time saving and cost effective using readily available materials arranged in the order of use. Further, many kits fail to provide a container, e.g., a drawstring bag, equipped with the materials needed to clean a patient and which can serve as a waste container after cleaning the patient. As an added problems, existing kits often fail to include a scent or odor eliminator or blocker to reduce or mask the smell associated with user waste.

A number of known devices which attempt to provide the user with a cleaning kit are, for various reasons, costly, inefficient, or burdensome. For example, U.S. Patent Pub. No. 2009/0014351 describes a prepackaged kit for cleaning an incontinent patient including an impermeable bag, disposable gloves, at least one cleaning cloth, and a skin care ointment. The prepackaged kit provides for quick disposal of the materials after the materials are used. As with many standard kits and methods of using the same, the kit and method fail to take into account a specific order of cleaning the patient, wherein the user is provided with a clean set of gloves and materials throughout the cleaning and changing steps. Such kit also fails to include a scent blocker to alleviate the unpleasant scent often experienced by the user, which also alleviates embarrassment experienced by the patient.

U.S. Pat. No. 4,917,238 describes a waste cleanup kit for cleaning up body substances while reducing the chances of infection from diseases carried by the substances. The cleanup kit includes an absorbent material, a disinfectant, a scoop, a glove, an absorbent towel, a hand wipe, and a plastic bag. In use, the kit is provided with a specific set of instructions for cleaning up the body substance using the absorbent material and scoop. The cleanup kit is not, for example, designed to quickly and inexpensively clean waste from a patient and thereafter clean the patient. In addition, the kit may only include one pair of gloves, which may become infected and dirty, thus making the gloves unsanitary for use during cleaning of the patient following the removal of a soiled garment, such as a diaper.

Therefore, a need exists to overcome the problems with the prior art as discussed above.

SUMMARY OF THE INVENTION

The invention provides a user-incontinence cleaning kit and method of use thereof that overcomes the hereinafore-mentioned disadvantages of the heretofore-known devices and methods of this general type and that provides a user with at least three pairs of gloves and at least three incontinence pads configured to be used in a sequential order to improve sanitation when cleaning a patient.

With the foregoing and other objects in view, there is provided, in accordance with the invention, a user-incontinence cleaning kit including at least one of a scent blocker and a facial mask, a plurality of gloves configured to be worn by a user in an overlapping relationship with respect to each other and corresponding to a select order of use for cleaning a patient, and a plurality of incontinence pads sized and shaped to be interposed between a backside of the patient and a top of a patient support structure.

In accordance with another feature, an embodiment of the present invention includes the user-incontinence cleaning kit further consisting of a set of three pairs of gloves.

In accordance with a further feature of the present invention, the scent blocker is one of a topical substance and an aloe.

In accordance with a further feature of the present invention, the plurality of incontinence pads are configured to be arranged in a sequential order of use for cleaning the patient.

In accordance with another feature of the present invention, the user-incontinence cleaning kit may include a bag for receiving the plurality of gloves and the plurality of incontinence pads and a collapsible cup sized to receive and dispose within the disposal bag a quantity of user waste from at least one of a first one of the incontinence pads and the patient.

In accordance with another feature, an embodiment of the present invention also includes the user-incontinence cleaning kit having a water-activated bathing cloth and a garment sized and shaped to couple to the patient.

In accordance with the present invention, a method of cleaning a patient using a user-incontinence cleaning kit is provided which may include providing a user-incontinence cleaning kit having a plurality of gloves sized to cover a user's hands and configured to be worn by the user in an overlapping relationship with respect to each other and corresponding to a select order of use for cleaning a patient and a plurality of incontinence pads sized and shaped to be interposed between a backside of a patient and a top of a patient support structure, coupling at least three pairs of gloves of the plurality of gloves over the user's hands in the select order of use for cleaning the patient, placing at least three incontinence pads of the plurality of incontinence pads in close proximity to the patient, moving the patient to a garment removal position and removing an existing garment from the patient, removing a first pair of the plurality of gloves from the user's hands and disposing of the first pair of the plurality of gloves and a first one of the least three incontinence pads, cleaning the patient, removing a second pair of the plurality of gloves from the user's hands and disposing of a second pair of the plurality of gloves and a second one of the least three incontinence pads, moving the patient to a garment application position, and removing a third pair of the plurality of gloves from the user's hands and disposing of the third pair of the plurality of gloves.

In accordance with another feature of the present invention, the method may include providing a scent blocker and a mask for receiving the scent blocker therein, the mask sized to cover a user's nostrils, placing a portion of the scent blocker within the mask, and coupling the mask to a user.

In accordance with a further feature of the present invention, the method may include placing the at least three incontinence pads of the plurality of incontinence pads between a backside of a patient and a top of a patient support structure.

In accordance with yet another feature of the present invention, the method may include providing a disposal bag and a collapsible cup, removing any user waste from at least one of the first one of the at least three incontinence pads and the patient using the collapsible cup, and inserting the first one of the at least three incontinence pads and the collapsible cup within the disposal bag.

In accordance with another feature of the present invention, the method may include applying at least one soothing substance on the user while wearing the third pair of the plurality of gloves.

In accordance with yet another feature of the present invention, the method may include placing a clean garment on the patient prior to removing the third pair of the plurality of gloves from the user's hands and disposing of the third pair of the plurality of gloves and the third one of the at least three incontinence pads.

In accordance with another feature of the present invention, the method may include placing a clean garment on the patient prior to removing the third pair of the plurality of gloves from the user's hands and disposing of the third pair of the plurality of gloves and the third one of the at least three incontinence pads.

In accordance with a further feature of the present invention, the method may include placing a clean garment on the patient after removing the third pair of the plurality of gloves from the user's hands and disposing of the third pair of the plurality of gloves and the third incontinence pad.

In accordance with the present invention, a method of cleaning a patient using a user-incontinence cleaning kit is provided which may include providing a user-incontinence cleaning kit having a plurality of gloves sized to cover a user's hands and configured to be worn by the user in an overlapping relationship with respect to each other and corresponding to a select order of use for cleaning a patient and a plurality of incontinence pads sized and shaped to be interposed between a backside of a patient and a top of a patient support structure, coupling the plurality of gloves over the user's hands in a sequential order of use for cleaning the patient, placing the plurality of incontinence pads in close proximity to the patient in the sequential order of use for cleaning the patient, moving the patient to a garment removal position including a first pair of the plurality of gloves and a first one of the plurality of incontinence pads in contact with the patient, removing the first pair of the plurality of gloves, cleaning the patient with a second pair of the plurality of gloves and a second one of the plurality of incontinence pads in contact with the patient, removing the second pair of the plurality of gloves, and moving the patient to a garment application position including a third pair of the plurality of gloves and a third one of the plurality of incontinence pads in contact with the patient.

In accordance with another feature of the present invention, the method may include providing a scent blocker and a mask for receiving the scent blocker therein, the mask sized to cover a user's nostrils, placing a portion of the scent blocker within the mask, and coupling the mask to a user.

In accordance with a further feature of the present invention, the method may include inserting the plurality of incontinence pads between a backside of a patient and a top of a patient support structure.

In accordance with another feature of the present invention, the garment removal position may include removing an existing garment and disposing of the existing garment, the first pair of the plurality of gloves and the first one of the plurality of incontinence pads in a waste container.

In accordance with another feature of the present invention, the method may include applying at least one soothing substance on the user while wearing the third pair of the plurality of gloves.

In accordance with yet another feature of the present invention, the method may include providing a disposal bag and a collapsible cup, removing any user waste from at least one of the first incontinence pad and the patient using the collapsible cup, and inserting the first one of the plurality of incontinence pads and the collapsible cup within the disposal bag.

In accordance with another feature of the present invention, the garment application position may include placing a clean garment on the patient.

Although the invention is illustrated and described herein as embodied in a user-incontinence cleaning kit and method of use it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to a direction of the compact case.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
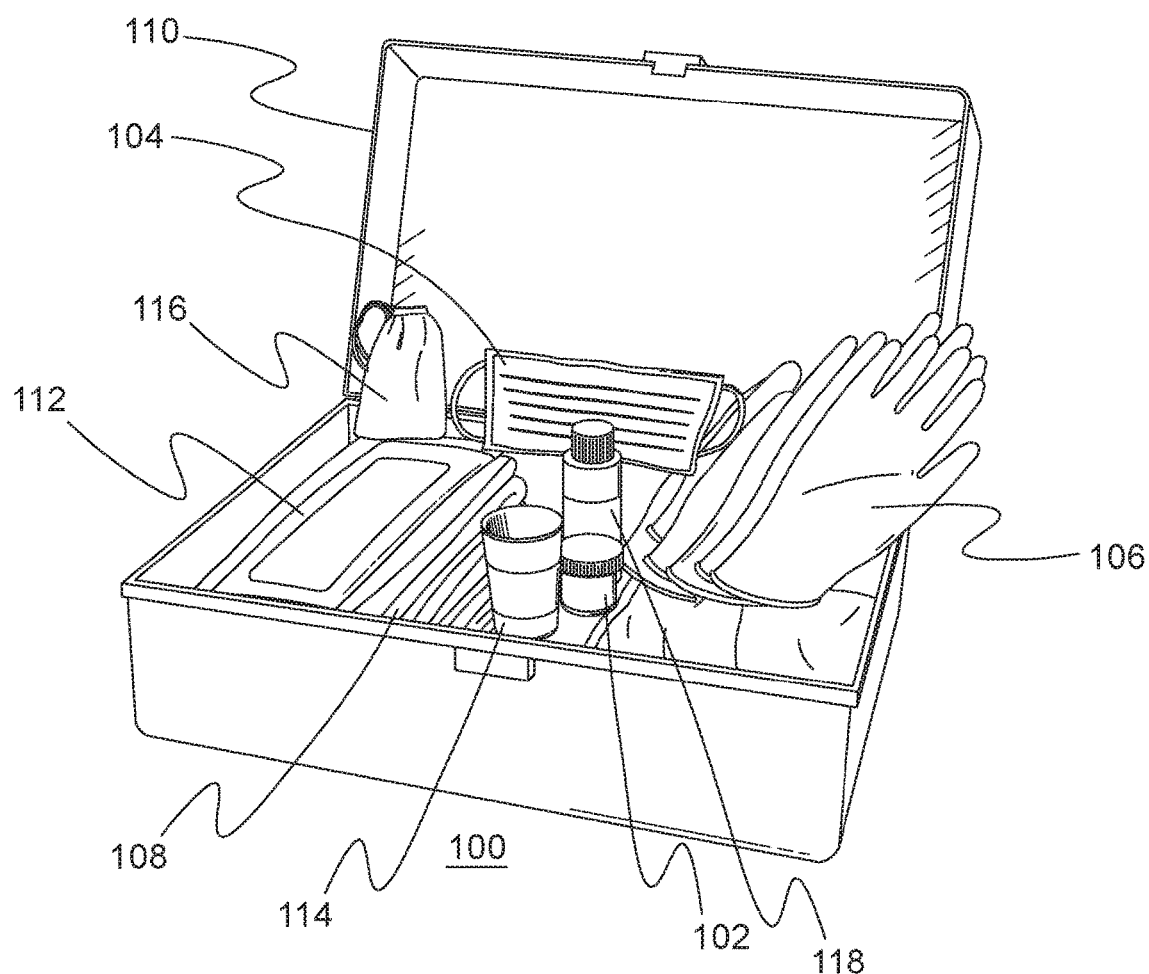
FIG. 1 is a perspective view of a user-incontinence cleaning kit including a number of exemplary contents used for quickly and effectively cleaning a patient in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient user-incontinence cleaning kit that includes the contents for a user to clean a patient after he or she has soiled himself or herself in a quick and effective manner. Embodiments of the invention provide the user-incontinence cleaning kit including at least three pairs of gloves and at least three incontinence pads arranged in a select order of use for cleaning the patient to improve sanitation when the gloves and incontinence pads are in contact with the patient. In addition, embodiments of the invention provide a scent blocker and a mask for receiving the scent blocker therein, the mask sized to cover a user's nostrils to reduce or mask the unpleasant odors associated with user waste and/or septic bedsores.

Referring now to FIG. 1, one embodiment of the present invention is shown in a perspective view. FIG. 1 shows several advantageous features of the present invention, but, as will be described below, the invention can be provided in several shapes, sizes, combinations of features and components, and varying numbers and functions of the components. The first example of a user-incontinence cleaning kit 100, as shown in FIG. 1, includes a scent blocker 102, a mask 104 for receiving the scent blocker therein, one or more pairs of gloves 106, and one or more incontinence pads 108. The kit 100 is not limited to the aforementioned items, and may have additional or less items in accordance with achieving the purpose of effectively cleaning a patient in a quick and efficient manner using the items supplied in the kit, as will be described in further detail herein.

In one embodiment, the kit 100 may be provided in a compact case 110 that is preferably lightweight so as to be easily carried by the user. The kit 100 is not limited to being provided in the case 110. Rather, in a preferred embodiment, the case 110 is a drawstring bag that may be used to initially supply the items for cleaning the patient to the user and which may also be used to discard one or more of the items after cleaning the patient. In other embodiments, the case 110 may be a basket or other container that may be easily and conveniently carried by the user. In another embodiment, the contents of the kit 100 may be manually carried by the user without the use of a case.

In one embodiment, the scent blocker 102 may be, without limitation, a topical substance, e.g., Tiger Balm®, an ointment, or another ambient substance for providing relief from or preventing the user from smelling the patient's waste or discharge. The use of the scent blocker 102 may also reduce the risk of patient embarrassment for cognizant patients. In use, in one embodiment, the scent blocker 102 may be placed in the mask 104 that is then placed on the user's head so as to cover the user's nostrils. In other embodiments, the scent blocker 102 may be applied to the user's skin or may be emitted within the air surrounding the user to provide relief from the undesirable smell of the patient's waste or discharge. In one embodiment, the mask 104 may be, without limitation, a standard hospital facial mask commonly found in a hospital setting. In this embodiment, the mask 104 may include a length of approximately 7-8 inches and a width of approximately 3-4 inches. In other embodiments, the length and width of the mask 104 may be outside of this range. In another embodiment, the mask 104 may be a scented mask, i.e., a scent blocker may be embedded in the mask.

Figure 2:
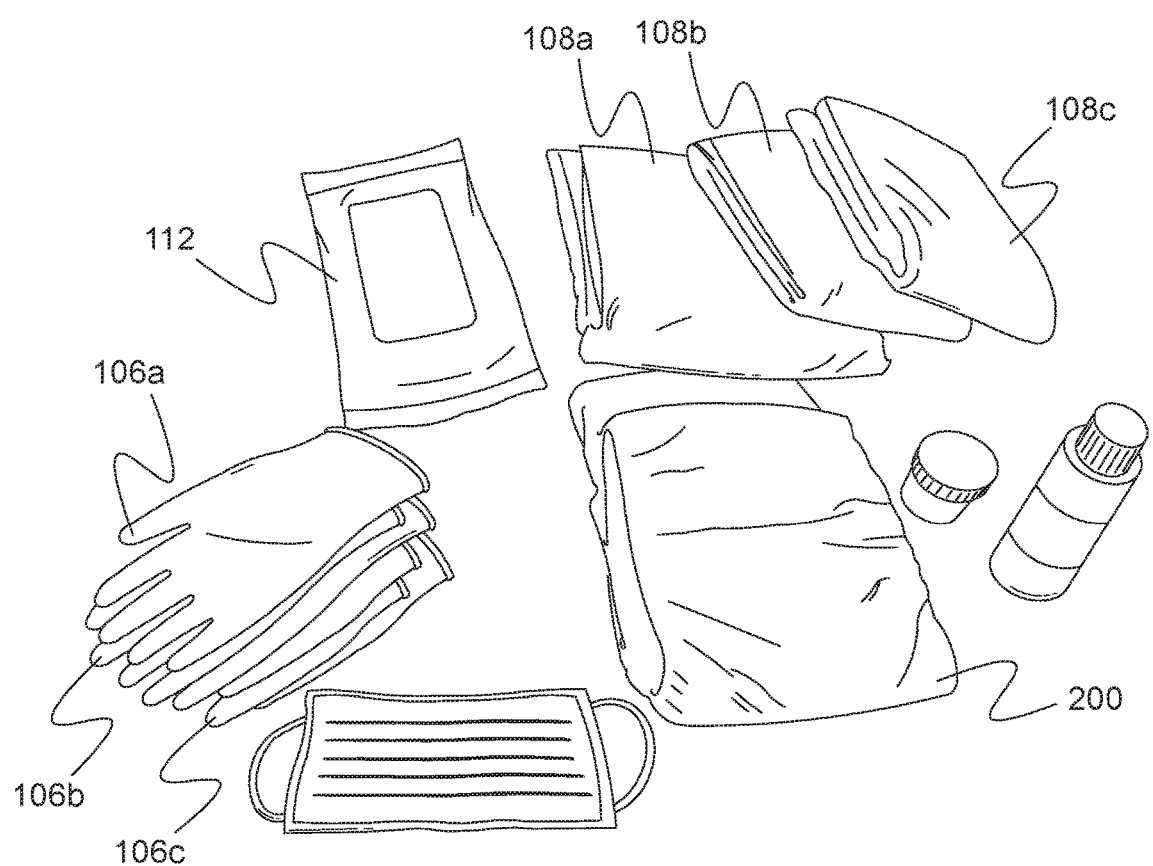
FIG. 2 is a perspective view depicting the exemplary contents of the user-incontinence cleaning kit of FIG. 1 including at least three pairs of gloves, an incontinence pad case, at least three incontinence pads, and a fresh sanitary garment in accordance with the present invention.
Figure 3:
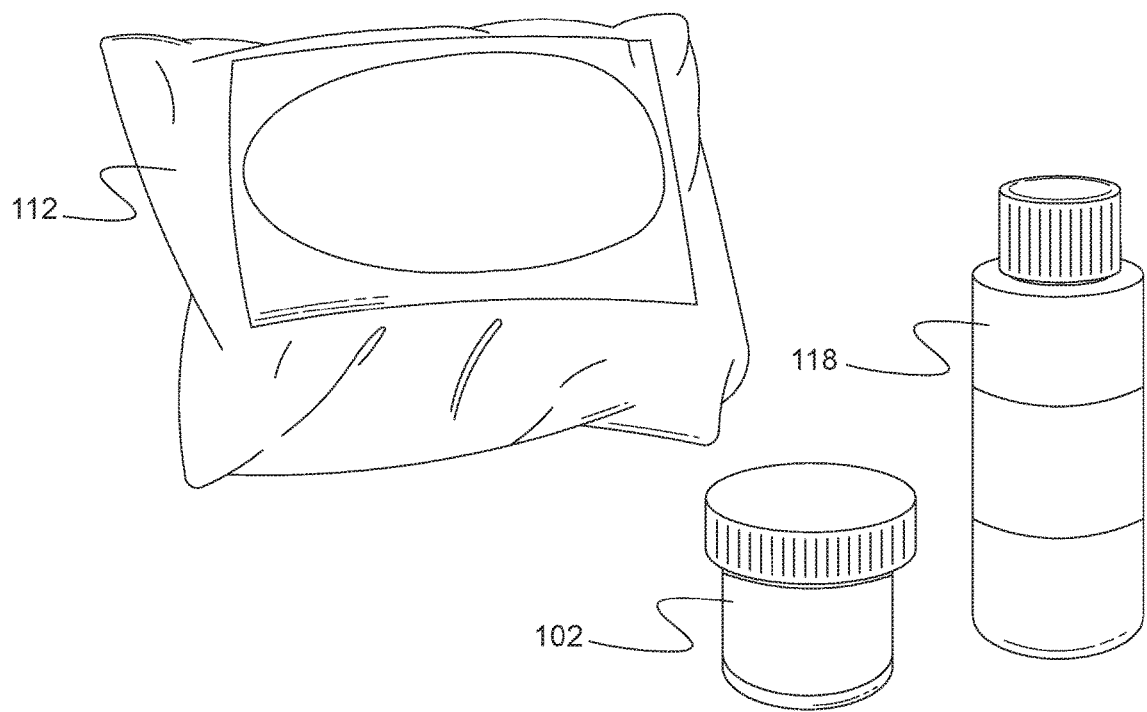
FIG. 3 is a perspective view of the contents of the user-incontinence cleaning kit of FIG. 1 including a scent blocker, the incontinence pad case, and a soothing substance in accordance with the present invention.
Figure 4:
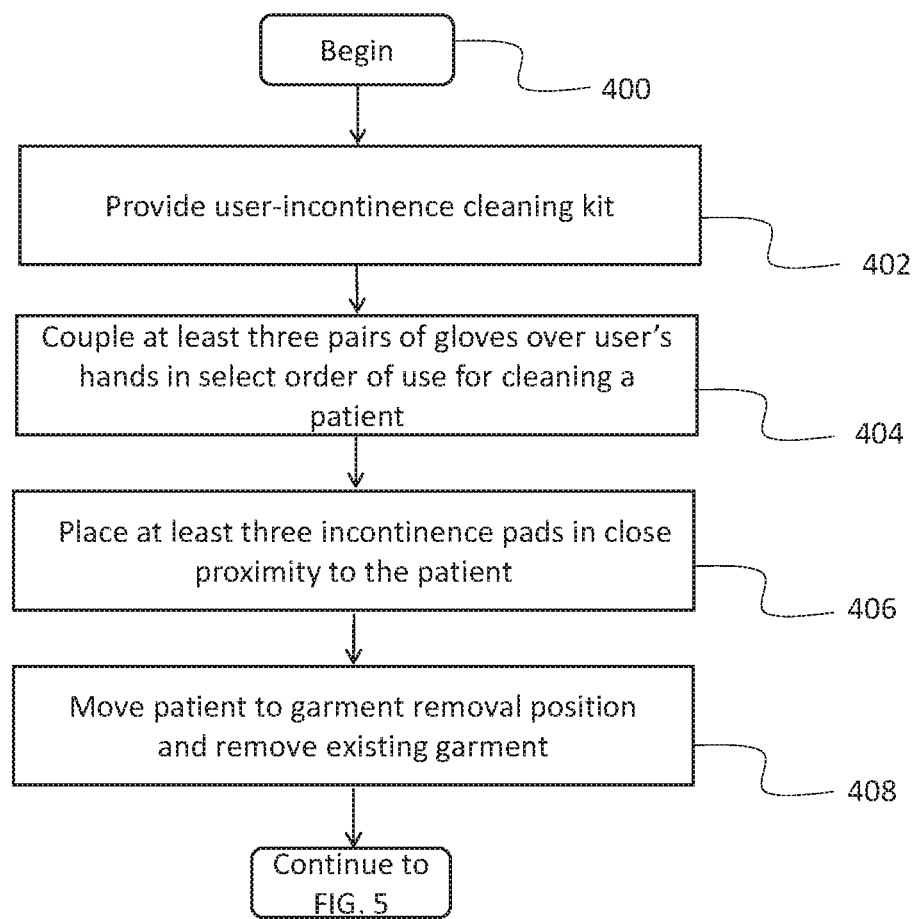
FIG. 4 is a process flow diagram depicting an exemplary method of using a user-incontinence cleaning kit.
Figure 5:
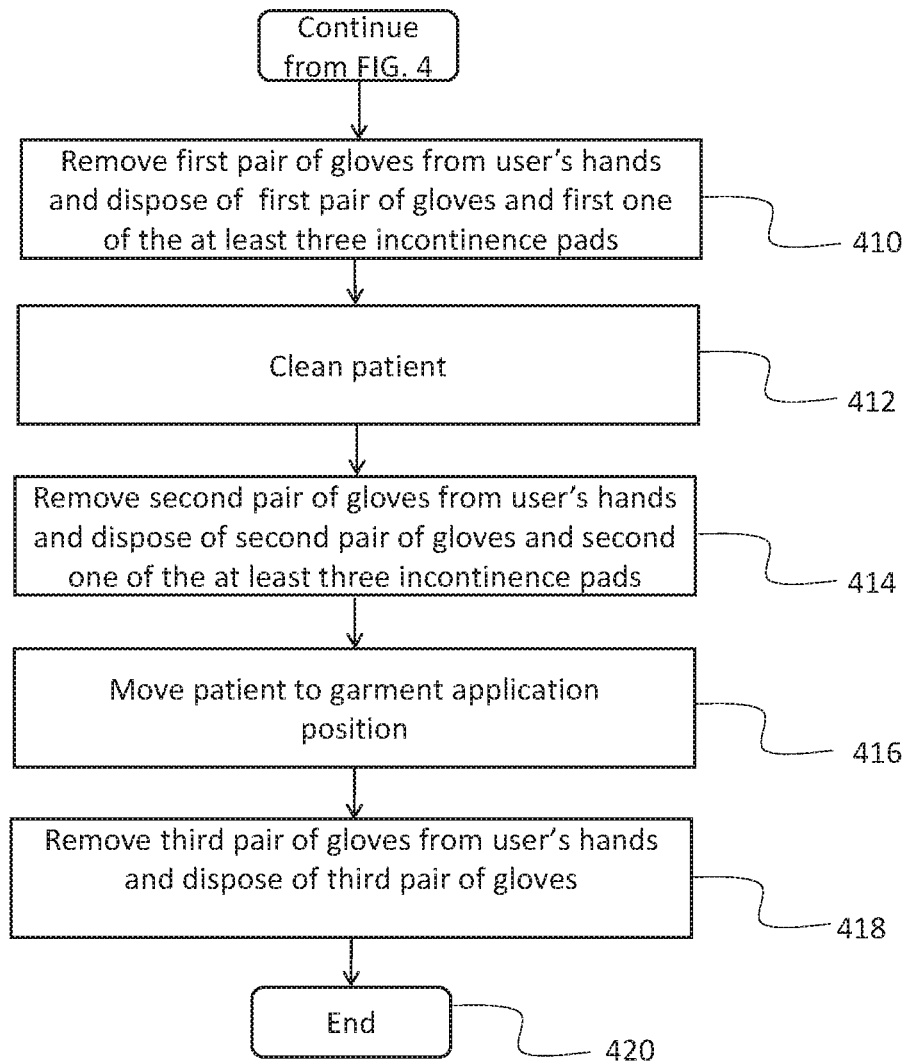
FIG. 5 is a continuation of the process flow diagram of FIG. 4 depicting the exemplary method of using a user-incontinence cleaning kit.

With reference to FIGS. 1-3, in conjunction with the process flow diagram of FIGS. 4 and 5, there is provided a method of using a user-incontinence cleaning kit, such as the a user-incontinence cleaning kit 100. The method is not limited to use with the user-incontinence cleaning kit 100 but may be used with other user-incontinence cleaning kits as well. Although FIGS. 4 and 5 show a specific order of executing the process steps, the order of executing the steps may be changed relative to the order shown in certain embodiments. Also, two or more blocks shown in succession may be executed concurrently or with partial concurrence in some embodiments. Certain steps may also be omitted in FIGS. 4 and 5 for the sake of brevity. In some embodiments, some or all of the process steps included in FIGS. 4 and 5 can be combined into a single process.

In one embodiment, the method begins at step 400 and moves directly to step 402, where a user-incontinence cleaning kit 100, which may be referred to herein as the kit 100, is provided by the user. In one embodiment, as mentioned above, the user-incontinence cleaning kit 100 may, but does not necessarily, include the scent blocker 102, the mask 104, one or more pairs of gloves 106a-n, and one or more incontinence pads 108a-n, where the indicator "n" is intended to represent any number greater than one. In a preferred embodiment, as best shown in FIG. 2, the kit 100 may include at least three pairs of gloves 106a-c, generally designated as a first pair of gloves 106a, a second pair of gloves 106b, and a third pair of gloves 106c. In the same vein, in the preferred embodiment, the kit 100 may also include at least three incontinence pads 108a-c, generally designated as a first incontinence pad 108a, a second incontinence pad 108b, and a third incontinence pad 108c. Naturally, the user may remove the items from the case 110. When the case 110 is a drawstring bag, the user may conveniently hang the drawstring bag on a side of the patient's bed so as to easily discard one or more items contained in the kit following the cleaning of the patient, as will be described further herein.

Advantageously, as shown in FIGS. 1-3, the incontinence pads 108a-c may be provided in a convenient incontinence pad case 112. In one embodiment, the incontinence pad case 112 may include three pre-packaged incontinence pads 108 therein. In other embodiments, the incontinence pad case 112 may include more or less than three incontinence pads 108a-c. The term "incontinence pad" is defined herein in its broadest possible sense as a substantially impermeable multi-layer sheet with absorbent properties. The incontinence pad may commonly be referred to as a mattress pad or a chuck.

With reference to FIGS. 2 and 4, the gloves 106a-c are sized to cover a user's hands and may be of any suitable material for cleaning a patient, e.g., latex, rubber, vinyl, neoprene or the like. In one embodiment, the gloves 106a-n include a circumference of approximately 7-8 inches when measured from below the user's knuckles. In another embodiment, the gloves 106a-n include a circumference of approximately 8-9 inches when measured from below the user's knuckles. In other embodiments, the gloves 106a-n may include a circumference that is less than 7 inches or greater than 9 inches. The user is generally intended by be an adult caretaker however the term "user" encompasses any individual tasked with taking care of an incontinent individual.

In step 404, the method may include coupling the gloves 106a, 106b, and 106c over the user's hands in an overlapping relationship with respect to each other and corresponding to a select order of use for cleaning a patient. Said another way, the present method includes the user placing the gloves 106a-n in a sequential order over the user's hands, such as placing the third pair of the gloves 106c directly over the user's hands, the second pair of the gloves 106b over the third pair of gloves 106c, and the first pair of gloves 106a over the second pair of gloves 106b. In this manner, the first pair of gloves 106a, intended to be used first by the user, are readily accessible as the uppermost pair of gloves 106. In one embodiment, before or after putting on the gloves 106a-n, the user may place a portion of the scent blocker 102 into the mask 104 and place the mask 104 over the user's head. The portion of the scent blocker 102 used may be based upon the user's preference.

In one embodiment, the method proceeds to step 406, which includes placing the first incontinence pad 108a, the second incontinence pad 108b, and the third incontinence pad 108c in close proximity to the patient. More specifically, in a preferred embodiment, the incontinence pads 108a-n are sized and shaped to be interposed between a backside of a patient and a top of a patient support structure and are arranged in the sequential order of use. The sequential order of use may include the first incontinence pad 108a stacked on top of the second incontinence pad 108b and the third incontinence pad 108c, with the third incontinence pad 108c closest to the patient support structure and the first incontinence pad 108a as the uppermost incontinence pad 108. The support structure may be any suitable structure for a patient to lay on, e.g., a mattress, a patient maneuvering device, etc.

In one embodiment, the incontinence pads 108a-n may be a generally rectangular shape. In other embodiments, the incontinence pads 108a-n may be, without limitation, square, round, oval, or another suitable shape for covering a portion, e.g., at least 50-75% of the structure disposed beneath the patient's buttocks. In the same vein, in one embodiment, the incontinence pads 108a-n may be of a length that is between approximately 36-40 inches and of a width between approximately 23-27 inches. In other embodiments, the length and the width may be outside of these ranges. The incontinence pads 108a-n may be placed under the patient while cleaning the patient and even before cleaning the patient, such as when the patient is in the bed-ridden position and not soiled. In other embodiments, the incontinence pads 108a-n may be within 3-4 inches of the patient for convenient access by the user.

In step 408, in one embodiment, the method includes moving the patient to a sanitary garment removal position to remove any existing garment from the patient. The term "garment" is defined herein in its broadest possible sense as a piece of absorbent material configured to absorb and retain patient discharge, e.g., a diaper. In a preferred embodiment, throughout step 408, the first pair of gloves 106a and the first incontinence pad 108a are in contact with the patient. The garment removal position may include rolling the patient on his or her hip to remove any clothing and/or the garment the patient may be wearing. Prior to rolling or otherwise moving the patient, the method may include the user obtaining a container with water to be used during cleaning of the patient. In the same vein, in one embodiment, step 406 of inserting the incontinence pads 108a-n underneath the patient, may occur after the patient is rolled on his or her hip. More specifically, with the patient rolled on his or her hip, the user may tuck the incontinence pads 108a-n underneath the patient, leaving the incontinence pads 108a-n in a partially rolled configuration. Thereafter, the user may turn the patient on his or her back and straighten out the incontinence pads 108a-n in a relatively planar configuration prior to cleaning the patient.

In one embodiment, as shown in FIG. 1, the kit 100 may include a cup 114 and a disposable bag 116. In one embodiment, the cup 114 is a collapsible cup that may be made of, without limitation, paper, plastic, polystyrene or another suitable material. The cup 114 may be used to scoop the patient waste off the first incontinence pad 108a and/or the patient. In another embodiment, a fecal waste scoop may be used to dispose of the patient waste. Thereafter, the garment may be removed from the patient.

After the garment is removed from the patient, via the patient being rolled on his or her hip, in step 410, the first pair of gloves 106a may be removed from the user's hands and disposed of in addition to the disposal of the soiled first incontinence pad 108a. In the same vein, the garment and the cup 114 may also be disposed by the user. In one embodiment, the disposal includes placing the contents in the disposable bag 116, which may be a drawstring or other disposal bag. In a preferred embodiment, the disposable bag 116 is the case 110 that originally provided the contents of the kit. In another embodiment, the disposable bag 116 may be re-usable. In other embodiments, disposal by the user may include placing the aforementioned items into a trash can or contaminant waste container.

In one embodiment, in step 412, the method includes cleaning, i.e., wiping, the patient. During step 412, advantageously, the user is now wearing a clean pair of gloves 106, i.e., the second pair of gloves 106b. In the same vein, to further increase sanitation, the second incontinence pad 108b, which is preferably underneath the patient, is also clean. In embodiments in which the second incontinence pad 108b is not already disposed underneath the patient, step 412 may include the second incontinence pad 108b being inserted underneath the patient.

In one embodiment, the process of cleaning the patient includes the user rolling the patient on his or her hip again and thereafter using a cloth, sponge, or the like to wipe any user waste from the patient. More specifically, the user may utilize a water-activated bathing cloth, used in connection with the water container, or at least one wet-wipe to wipe the patient's backside. In another embodiment, the user may clean the patient using soap and water in connection with a bathing cloth or other suitable cleaning device. In other embodiments, the user may use one or more pre-moistened wipes to clean the patient. For example, in one embodiment, approximately 8-10 pre-moistened wipes may be used for fecal incontinence and approximately 5-8 pre-moistened wipes may be used for urinary incontinence. In one embodiment, a patient maneuvering apparatus may be used to roll or otherwise move the patient.

In one embodiment, the method continues to step 414 which may include the user removing the second pair of gloves 106b from the user's hands and removing the second incontinence pad 108b from underneath the user for disposal. In one embodiment, similar to disposal of the first pair of gloves 106a and the first incontinence pad 108a, the disposal may include placing the second pair of gloves 106b and the second incontinence pad 108b in the disposable bag 116 or into a trash can or contaminant waste container.

In one embodiment, the method continues to step 416 which may include moving the patient to a garment application position wherein the patient is again rolled on his or her hip. In a preferred embodiment, the garment application position includes the third set of gloves 106c and the third incontinence pad 108c now in contact with the patient. In embodiments in which the third incontinence pad 108c is not already disposed underneath the patient, the third incontinence pad 108c may be inserted underneath the patient.

In one embodiment, while the patient is again rolled on his or her hip, the method includes the user placing at least one soothing substance 118 on any effected or soiled areas of the patient, such as on or near the patient's buttocks. The soothing substance 118 may be an aloe, a gel, a cream or another soothing substance 118 intended to provide relief to the patient, such as when the patient has developed bed sores. With reference to FIG. 3, the soothing substance 118 may be provided in a different bottle than that housing the scent blocker 102 so that a user can easily and conveniently distinguish the two items when changing and cleaning the patient. In other embodiments, the scent blocker 102 may be the same substance as the soothing substance 118. In one embodiment, warm saline water may be applied to any existing sores on the patient's buttocks using a bottle, e.g., a spray bottle.

In one embodiment, step 418 may include the third pair of gloves 106n being removed from the user's hands for disposal. Similar to the disposal of the first and seconds pairs of gloves 106a, 106b, the disposal may include placing the contents in the disposable bag 116 or into a trash can or contaminant waste container. In a preferred embodiment, third incontinence pad 108c remains disposed underneath the patient until the next time the patient is cleaned. In other embodiments, the third incontinence pad 108c may be disposed of by the user.

With reference to FIG. 2, in conjunction with the flow diagram of FIG. 5, in one embodiment, following the removal of the third pair of gloves 106c, a fresh garment 200 may be placed on the patient. As such, the patient is provided with a fresh garment 200 that has not been exposed to any possible containments that may have been on the third pair of gloves 106c. In this embodiment, the user may choose to wear another pair of preferably clean gloves 106 or may apply the fresh garment 200 to the patient using bare hands. In another embodiment, the method may include the user placing the fresh garment 200 on the patient prior to removing the third pair of gloves 106c from the user's hands and disposing of the third pair of gloves 106c. In any event, following the application of the fresh garment 200, the user may insert three new incontinence pads 108a-c underneath the patient for future cleaning or the third incontinence pad 108c may remain underneath the user as explained above. In other embodiments, the three new incontinence pads 108a-c may be placed in close proximity to the patient and thereafter inserted under the patient while using the kit 100. The method ends at step 420.

A user-incontinence cleaning kit and method of use has been disclosed that provides the user with at least three pairs of gloves and at least three incontinence pads arranged in a select order of use for cleaning the patient to improve sanitation when the gloves and incontinence pads are in contact with the patient. Advantageously, the user-incontinence cleaning kit also provides the user with the items needed to quickly and effectively clean the patient without having to search for such items.

What is claimed is:
1. A user-incontinence cleaning kit comprising:
   a scent blocker;
   a facial mask;
   consisting of six separate gloves disposed in the kit and making a first pair, a second pair, and a third pair, the three pairs of gloves operably configured to be worn by each hand of the user in an overlapping relationship with respect to each other and corresponding to a select order of use for cleaning the patient and sequential removal when a patient is in a bed-ridden position;
   consisting of three incontinence pads having a folded configuration and operably configured, sized, and shaped to have an unfolded configuration that is at least 36 inches in length and 23 inches in width to cover a portion of a patient support structure in a planar configuration when a patient is in a bed-ridden position, wherein the bed-ridden position of the patient includes the three incontinence pads interposed between a backside of the patient and a top of a patient support structure and arranged in the sequential order for removal from the patient support structure corresponding in removal to the sequential removal of the three pairs of gloves from each hand of the user;
   a cup sized to receive a quantity of user waste from at least one of the plurality of incontinence pads and the patient; and
   a drawstring bag in which the scent blocker, three pairs of gloves, three incontinence pads, and cup are initially disposed, and which is configured to receive the three pair of gloves and the three incontinence pads upon the three pairs of gloves and three incontinence pads being soiled, wherein the drawstring bag is further configured to hold the soiled three pairs of gloves and soiled incontinence pads for later disposal.

2. The user-incontinence cleaning kit according to claim 1, further comprising:
   a soothing substance selected from the group consisting of an aloe, a gel, and a cream.

3. The user-incontinence cleaning kit according to claim 1, wherein:
the scent blocker is provided in the facial mask.

4. The user-incontinence cleaning kit according to claim 1, further comprising:
a bathing cloth; and
a garment sized and shaped to couple to the patient.

* * * * *